US011215560B2

(12) United States Patent
Scott (10) Patent No.: US 11,215,560 B2
(45) Date of Patent: Jan. 4, 2022

(54) PORTABLE BIOMARKER READER (71) Applicant: COM DEV LTD., Mississauga (CA)

(72) Inventor: Alan Scott, Arnprior (CA)

(73) Assignee: COM DEV Ltd., Mississauga (CA)

( * ) Notice: Subject to any disclaimer, the term of this patent is extended or adjusted under 35 U.S.C. 154(b) by 307 days.

(21) Appl. No.: 16/100,881

(22) Filed: Aug. 10, 2018

(65) Prior Publication Data
US 2020/0049626 A1 Feb. 13, 2020

(51) Int. Cl.
*G01N 21/64* (2006.01)
*G01N 21/25* (2006.01)
*G01N 21/62* (2006.01)
*F21V 8/00* (2006.01)
*A61B 5/00* (2006.01)
*G01N 33/50* (2006.01)

(52) U.S. Cl.
CPC ......... *G01N 21/645* (2013.01); *A61B 5/0071* (2013.01); *G01N 21/253* (2013.01); *G01N 21/6452* (2013.01); *G02B 6/0086* (2013.01); *G01N 33/5091* (2013.01)

(58) Field of Classification Search
None
See application file for complete search history.

(56) References Cited

U.S. PATENT DOCUMENTS

| 7,524,672 | B2  | 4/2009  | West et al. |            |
|-----------|-----|---------|-------------|------------|
| 8,344,333 | B2* | 1/2013  | Lu          | G01N 21/648 |
|           |     |         |             | 250/458.1  |
| 2003/0231309 | A1* | 12/2003 | Fulghum, Jr. | G01N 15/0205 |
|           |     |         |             | 356/338    |
| 2006/0093254 | A1* | 5/2006  | Mozdy       | G01N 21/253 |
|           |     |         |             | 385/12     |
| 2008/0056950 | A1* | 3/2008  | Weisbuch    | G01N 21/6452 |
|           |     |         |             | 422/82.11  |
| 2012/0021525 | A1* | 1/2012  | Fehr        | G01N 21/6452 |
|           |     |         |             | 436/94     |
| 2017/0343474 | A1  | 11/2017 | Hunter      |            |

OTHER PUBLICATIONS

"Alexa Fluor Dyes: Simply the Best", in Chapter 1, Molecular Probes Handbook, ThermoFisher Scientific, pp. 20-35, accessed May 2018.
"Our Technology", Sensoreal, webpage accessed Feb. 2018 <http://www.sensoreal.com/technology>.

* cited by examiner

*Primary Examiner* — Neil N Turk
(74) *Attorney, Agent, or Firm* — Bereskin & Parr LLP/S.E.N.C.R.L., s.r.l.; Isis E. Caulder; T. Cameron Gale (57) ABSTRACT

A portable imaging apparatus and system. A sample processing device has a reaction chamber configured to receive a sample and react the sample with a fluorescent compound that emits a specified wavelength of light when excited by light within an excitation band. An illumination source can be positioned to illuminate the reaction chamber when the sample processing device is positioned for imaging. A light guide can be positioned to face the reaction chamber and transfer the emitted light to an imaging detector. The light guide has a filter that blocks the wavelength of light from the illumination source and passes the fluorescent emitted light. The light guide unit defines an angular light acceptance range and is configured to constrain angular spreading of light.

22 Claims, 6 Drawing Sheets

PORTABLE BIOMARKER READER

FIELD

This disclosure relates generally to portable testing systems, and in particular to portable imaging-based testing systems.

INTRODUCTION

The following is not an admission that anything discussed below is part of the prior art or part of the common general knowledge of a person skilled in the art.

Biological samples from a subject, such as blood, saliva or urine, can be tested to identify the presence of one or more biomarkers. Biomarkers can be identified from the chemical constituents of the samples being tested. The identified biomarkers may provide an indication that the subject has one or more conditions.

Testing systems for identifying biomarkers are useful in a variety of situations. For instance, saliva or blood testing systems may be used to identify biomarkers such as drug residues in suspected impaired drivers. Biological analysis systems may also be used to test for biomarkers indicative of numerous diseases.

U.S. Pat. No. 7,524,672 of West et al. purports to disclose systems that include a manifold in fluid communication with a microfluidic chip having a microarray, an illuminator, and a detector in optical communication with the microarray as well as methods for using these systems for biological detection.

United States Patent Application Publication No. 2017/0343474 of Hunter purports to disclose a portable in-vitro (PIV) diagnostic detector operable to perform a fluorescence assay on a sample in one or more detection chambers of a cartridge is provided. The PIV diagnostic detector comprises a first optical module which includes (i) an LED light source for emitting substantially monochromatic light to illuminate a detection zone associated with at least one detection chamber; (ii) an excitation filter interposed between said light source and said detection zone; (iii) a light detector operable to detect fluorescent light emitted by an excited fluorescent label associated with the sample and to measure an intensity of the fluoresced light; and (iv) an emission filter interposed between said light detector and said detection zone. The (PIV) diagnostic detector further comprises a microprocessor operable to process the measured intensity of the fluoresced light to determine whether an analyte is present in the sample; wherein the first optical module is configured such that a longitudinal axis of the light source extends at an oblique angle with respect to a longitudinal axis of the light detector.

SUMMARY

The following introduction is provided to introduce the reader to the more detailed discussion to follow. The introduction is not intended to limit or define any claimed or as yet unclaimed invention. One or more inventions may reside in any combination or sub-combination of the elements or process steps disclosed in any part of this document including its claims and figures.

In accordance with a broad aspect of this disclosure, there is provided an imaging system that includes a sample processing device having at least one reaction chamber configured to receive a sample and a fluorescent compound usable to react with the sample, where the fluorescent compound is excitable by light with a wavelength that falls within an excitation band and the fluorescent compound emits light with a wavelength in an emission band in response to being excited; an illumination source optically coupled to the sample processing device, the illumination source operable to emit excitation light having an excitation wavelength that falls within the excitation band, where the illumination source and the sample processing device are arranged to direct at least a portion of the excitation light to the reaction chamber; an imaging detector operable to measure the intensity of received light; and a light guide unit having a first end optically coupled to the reaction chamber, a second end optically coupled to the imaging detector, and an optical filter located between the reaction chamber and the imaging detector; where the light guide unit defines an angular light acceptance range and is configured to constrain angular spreading of light entering the first end of the light guide unit; and the optical filter is configured to block light having the excitation wavelength that is emitted within the angular light acceptance range while passing light within at least a portion of the emission band.

In some embodiments, the imaging detector includes an array that defines a plurality of distinct spatial areas, and the imaging detector is operable to measure the intensity of received light in each of the spatial areas.

In some embodiments, the light guide unit includes an array of fiber-optic cables that extend from the first end to the second end, and each fiber-optic cable corresponds to one of the distinct spatial areas.

In some embodiments, the at least one reaction chamber includes a plurality of spaced apart reaction chambers; and each reaction chamber has at least one fiber-optic cable facing that reaction chamber at the first end of the light guide unit.

In some embodiments, the light guide unit includes an array of fiber-optic cables that extend from the first end to the second end. In some embodiments, each fiber-optic cable has a numerical aperture that is defined to allow light to enter the fiber-optic cables only from an angle of less than about 20 degrees.

In some embodiments, the optical filter includes a Bragg filter embedded in each fiber-optic cable.

In some embodiments, the optical filter includes multiple layers of optical coatings.

In some embodiments, the optical filter has a thickness of less than about 20 micrometers.

In some embodiments, the light guide unit includes a photonic crystal that extends from the first end to the second end.

In some embodiments, the emission band and the excitation band partially overlap; and the passband of the optical filter is defined to exclude the excitation band peak and excludes a portion of the emission band.

In some embodiments, the optical filter is provided at the first end of the light guide unit.

In some embodiments, the optical filter is also provided at the second end of the light guide unit.

In some embodiments, the at least one reaction chamber includes a plurality of spaced apart reaction chambers, and the light guide unit is configured to constrain the angular spreading of light emitted from each reaction chamber within the angular light acceptance range to prevent the overlap of light from adjacent chambers.

In some embodiments, the sample processing device includes a microfluidic chip.

In some embodiments, the filter is provided on a surface of the reaction chamber facing the light guide unit.

In some embodiments, the first end of the light guide unit is optically coupled to the reaction chamber on a front side of the sample processing device and the illumination source is optically coupled to a lateral side of the sample processing device.

In some embodiments, the first end of the light guide unit is detachably attached to the reaction chamber.

In accordance with another broad aspect of this disclosure, there is provided a portable imaging apparatus usable with a sample processing device that has a reaction chamber configured to receive a sample and a fluorescent compound usable to react with the sample, where the fluorescent compound is excitable by light with a wavelength that falls within an excitation band and the fluorescent compound emits light with a wavelength in an emission band in response to being excited. The portable imaging apparatus includes an imaging detector operable to detect an intensity of light incident on an input side of the imaging detector; an illumination source operable to emit excitation light having an excitation wavelength that falls within the excitation band; and a light guide unit extending from a first end to a second end that is optically coupled to the input side of the imaging detector, the light guide unit defining an angular light acceptance range and being configured to constrain angular spreading of light entering the first end of the light guide unit; where the light guide unit includes an optical filter configured to block light having the excitation wavelength that is emitted within the angular light acceptance range while passing light within at least a portion of the emission band; and the portable imaging apparatus is arranged to receive the sample processing device with the first end of the light guide unit optically coupled to the reaction chamber and the illumination source positioned to direct at least a portion of the excitation light to the reaction chamber.

In some embodiments, the imaging detector includes an array that defines a plurality of distinct spatial areas, and the imaging detector is operable to measure the intensity of received light in each of the spatial areas.

In some embodiments, the light guide unit includes an array of fiber-optic cables that extend from the first end to the second end, and each fiber-optic cable corresponds to one of the distinct spatial areas.

In some embodiments, the light guide unit includes an array of fiber-optic cables that extend from the first end to the second end. In some embodiments, the fiber-optic cables have a numerical aperture that is defined to allow light to enter the fiber-optic cables only from an angle of less than about 20 degrees.

In some embodiments, the optical filter includes a Bragg filter embedded in each fiber-optic cable of the light guide unit.

In some embodiments, the optical filter includes multiple layers of optical coatings.

In some embodiments, the coatings are provided on the first end of the light guide unit.

In some embodiments, the coatings are also provided on the second end of the light guide unit.

In some embodiments, the light guide unit includes a photonic crystal that extends from the first end to the second end.

In some embodiments, the optical filter has a thickness of less than about 20 micrometers.

In some embodiments, the at least one reaction chamber includes a plurality of spaced apart reaction chambers, and the light guide unit is configured to constrain the angular spreading of light emitted from each reaction chamber within the angular light acceptance range to prevent the overlap of light from adjacent chambers.

In some embodiments, the portable imaging apparatus is arranged to receive the sample processing device with the first end of the light guide unit optically coupled to the reaction chamber on a front side of the sample processing device and the illumination source optically coupled to a lateral side of the sample processing device.

It will be appreciated by a person skilled in the art that an apparatus system, or method disclosed herein may embody any one or more of the features contained herein and that the features may be used in any particular combination or sub-combination.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which.

The drawings included herewith are for illustrating various examples of articles, methods, and apparatuses of the teaching of the present specification and are not intended to limit the scope of what is taught in any way.

DESCRIPTION OF EXAMPLE EMBODIMENTS

Various apparatuses, methods and compositions are described below to provide an example of an embodiment of each claimed invention. No embodiment described below limits any claimed invention and any claimed invention may cover apparatuses and methods that differ from those described below. The claimed inventions are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed invention. Any invention disclosed in an apparatus, method or composition described below that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more parts are said to be "coupled", "connected", "attached", or "fastened" where the parts are joined or operate together either directly or indirectly (i.e., through one or more intermediate parts), so long as a link occurs. As used herein and in the claims, two or more parts are said to be "directly coupled", "directly connected", "directly attached", or "directly fastened" where the parts are connected in physical contact with each other. None of the terms "coupled", "connected", "attached", and "fastened" distinguish the manner in which two or more parts are joined together.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

Embodiments described herein relate generally to systems and apparatus for testing biological samples. In particular, the systems and apparatuses described herein relate to imaging-based testing of biological samples that are treated with light emitting compounds such as fluorophores. The systems and apparatuses described herein may enable the implementation of compact, portable image-based testing systems and devices.

Biological samples can be acquired using a sample processing device, such as a microfluidic chip. These biological samples can be brought into contact with fluorescent compounds that are configured to dye or label specific cells, tissues or biomolecules of interest. For instance, the fluorescent compounds may be fluorescent dyes that are conjugated to antibodies that target biomolecules of interest. The sample processing device can include one or more reaction chambers in which the acquired sample is reacted by the fluorescent compounds.

The fluorescent compounds can be selected to emit light in response to excitation by a defined wavelength of light. In order to evaluate the presence of biomarkers in the biological samples, the processed sample (after reacting with the fluorescent compound) can be illuminated by light having a wavelength within the excitation band of the fluorescent compound.

The portions of the processed sample that have been labelled by the fluorescent compound can emit light. The fluorescent compound emits light with a wavelength that falls within a known emission band. The intensity of the emitted light can then be measured in order to evaluate the concentration of the biomarker of interest.

Embodiments of the systems and apparatuses described herein may provide portable detection devices usable to evaluate the presence of a biomarker of interest. The detection apparatus can include an imaging detector that is operable to measure the intensity of light emitted from a sample processing device. For instance, a CCD or CMOS imager may be used as the imaging detector.

The detection apparatus can also include a light guide unit. The light guide unit can be attached to a sample collection or processing device that has one or more reaction chambers. The light guide unit can guide light emitted from the sample processing device to the imaging detector.

The light guide unit can also be configured to restrict the light that reaches the imaging detector and how light entering the light guide unit travels. For instance, the light guide unit may define an angular light acceptance range. The angular light acceptance range may define a range of incidence angles across which light is able to enter the light guide unit. The light guide unit may prevent light from entering, and passing through, the light guide unit if it is incident on the light guide unit at an angle outside of the angular light acceptance range.

The light guide unit may also restrict the spread of light that passes therethrough. The sample processing device may include a plurality of reaction chambers, each of which may emit light. The light guide unit may be configured to restrict the angular spread of light as it passes through the light guide unit to prevent light from adjacent reaction chambers from overlapping (or to at least reduce overlap). This may ensure that the imaging detector can identify differences in light intensity between different reaction chambers.

For example, the light guide unit may include a fiber-optic array with a plurality of optical fiber cables (also referred to herein as fiber-optic cables). The fiber-optic cables can have a first end facing the imaging detector and a second end that is arranged to face a sample processing device. Each fiber optic cable can pass light that enters from the first end to the second end. The light can pass then to the imaging detector from the second end of each fiber optic cable. The light that enters an individual fiber optic cable can be prevented from overlapping with light in adjacent fiber-optic cables.

The fiber-optic cables may be selected with a numerical aperture that defines the angular light acceptance range. For instance, the numerical aperture of the fiber-optic cables can be defined to allow light to enter the fiber-optic cables from an angle of about 20 degrees or less. This may help ensure that the light guide unit controls the light that is emitted therethrough.

In some cases, the sample processing device may include a plurality of reaction chambers. Each fiber-optic cable can face one of the reaction chambers of the sample processing device. The width of the fiber optic cables may be substantially less than the width of the emission windows of each reaction chamber (as well as less than the spacing between adjacent reaction chambers). Accordingly, each fiber-optic cable may receive light from only one reaction chamber. The fiber-optic cables may thus prevent light from different reaction chambers from overlapping as the light travels from the first end to the second end.

The imaging detector may also define an array of spatial detection regions. Each spatial detection region may be coupled to one or more of the fiber-optic cables. In some cases, each fiber-optic cable can be arranged to face only one of the spatial detection regions. Each spatial detection region may thus detect the intensity of light emitted from a single reaction chamber.

In order to assess the presence of the biomarkers in the reaction chambers, the fluorescent compounds can be excited using an excitation light signal. The detection apparatus can include an illumination source configured to emit an excitation light signal.

The illumination source can be positioned to illuminate the sample processing device when it is positioned in proximity to, or contacting, the light guide unit.

The wavelength of the light emitted by the illumination source can be selected to be within the excitation bandwidth of the fluorescent compound used in the sample processing device.

In order to provide an accurate assessment of the biomarker's presence in the sample(s) being tested, the detection apparatus can be configured to reduce the amount of excitation light (from the illumination source) that is captured by the imaging detector. The detection apparatus can include an optical filter configured to prevent the excitation light from reaching the imaging detector. The filter can be configured with a high optical depth in the excitation band of the illumination source (i.e. strong blocking of the excitation band).

In some embodiments described herein, the light guide unit may include an optical coating that defines the optical filter. The optical coating can include layers of dielectric and/or metallic coatings with different refractive indices. The refractive indices of the coating layers can be selected so that the interfaces between the coating layers selectively cause constructive interference for the wavelengths of interest (i.e. some or all of the emission band of the fluorescent compound) while destructively interfering the undesired wavelengths (i.e. the excitation band of the illumination source). The thickness and number of coating layers deposited can be controlled to define the passband of the optical filter.

In some cases, the optical coatings may be deposited directly on one or both ends of the optical fibers. In other cases, the optical coatings may be deposited on the reaction chambers and/or the imaging detector.

The plurality of optical fibers and the optical coating can form an integrated light guide unit or faceplate usable to transfer the emitted light from the sample processing device to the imaging detector. In some cases, rather than an optical coating, each optical fiber may include a Bragg grating that defines the optical filter. This may also provide the light guide unit as an integrated transmission and filtering faceplate. In such cases, the coating layers may be omitted.

In yet other cases, the light guide unit may include a photonic crystal. The photonic crystal may be configured to define the angular light acceptance range and optical filter.

The sample processing device can be connected to the imaging apparatus with the one or more reaction chambers in contact with the light guide unit. The light emitted from the fluorescent compound can then transfer directly through the light guide unit to the imaging detector. The imaging detector may then measure the intensity of the emitted light to evaluate the presence of one or more bio-markers. The light guide unit can control the wavelengths of light that are passed to the imaging detector, to reduce the pollution that might be caused by the excitation light.

Figure 1:
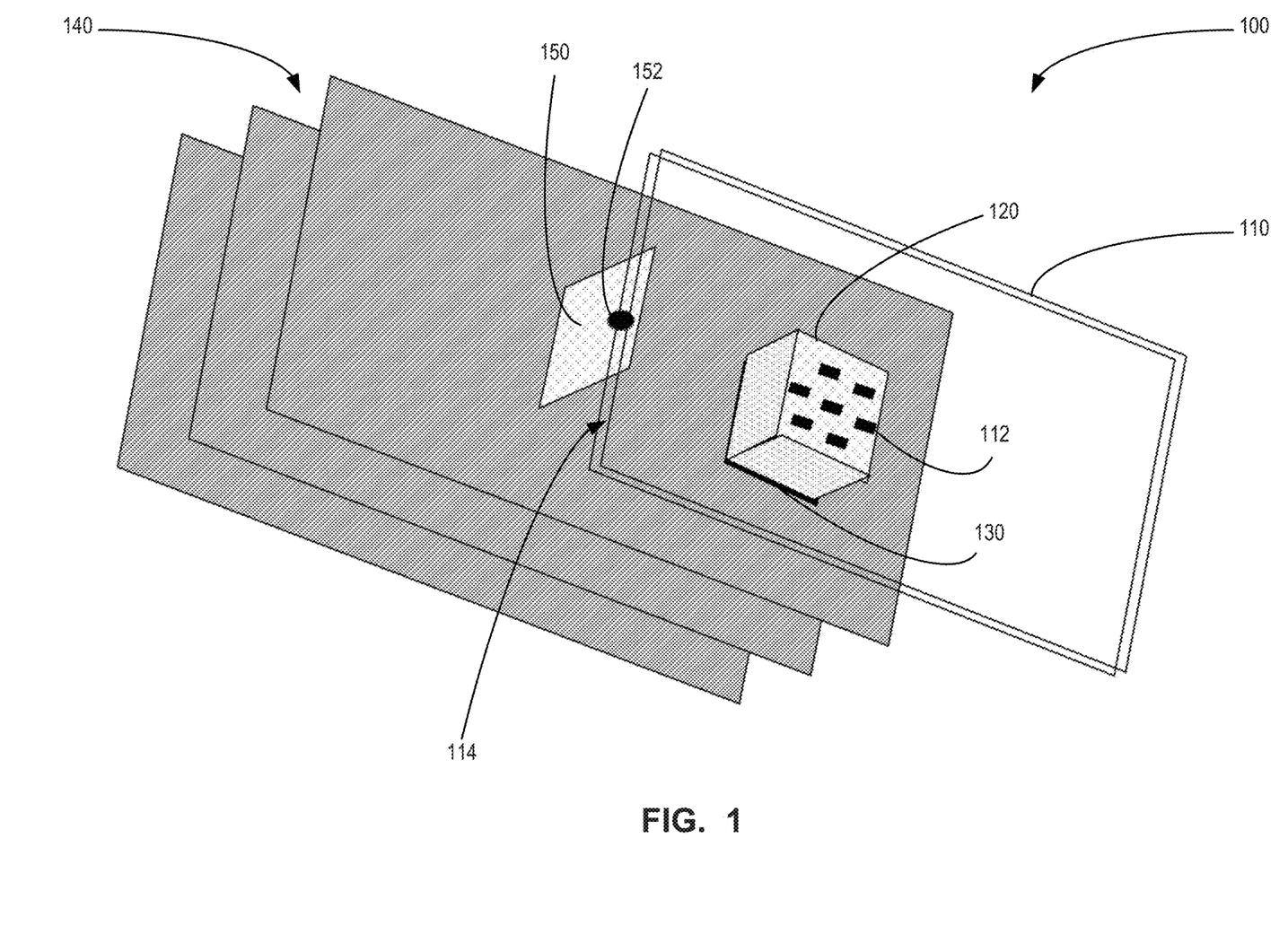
FIG. 1 is an exploded perspective view of an example imaging system in accordance with an embodiment.
Figure 2:
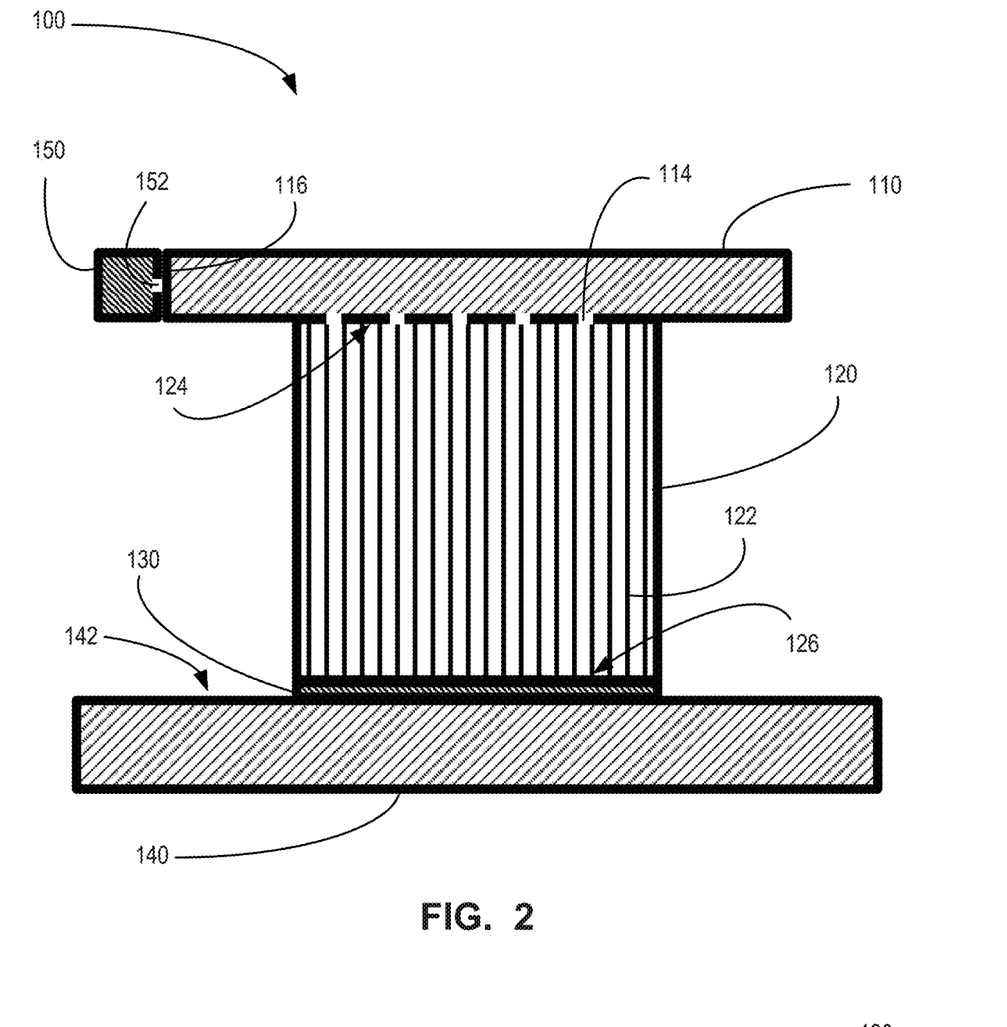
FIG. 2 is a sectional side view of the imaging system of FIG. 1.
Figure 3:
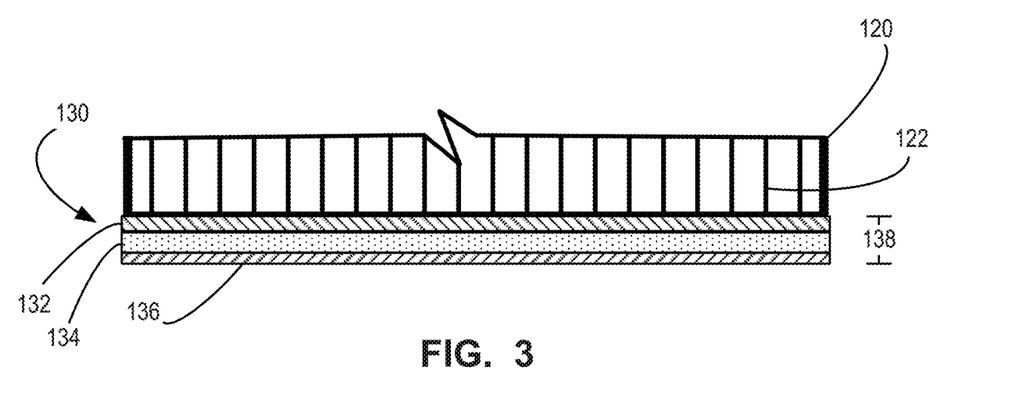
FIG. 3 is a partial sectional side view of an example light guide unit that may be used in the imaging system of FIG. 1.

Referring to FIGS. 1 to 3, an exemplary embodiment of an imaging system is shown generally as 100. In the illustrated embodiment, the imaging system 100 includes an imaging detector 140 that is connected to a light guide unit 120. The system 100 also include an illumination source 150. The illumination source 150 can emit light with a specified wavelength.

A sample processing device 110 is shown attached to the light guide unit 120. The sample processing device 110 can be configured to receive one or more biological samples to be tested.

The sample processing device 110 includes one or more reaction chambers 112. A fluorescent compound can be provided in each reaction chamber 112 to react with a received sample. The fluorescent compound can be configured to mark substances of interest in the received sample, such as biomarkers for disease or drug residue. For instance, the fluorescent compound may be conjugated with biomarker specific antibodies. When a sample is introduced into the reaction chamber 112, the fluorescent compound may then bond to the corresponding biomarker.

In some embodiments, the sample processing device 110 can include a plurality of reaction chambers 112. As shown in FIG. 1, the sample processing device 110 may include a matrix or array of reaction chambers 112, in this case seven reaction chambers 112. In some cases, the reaction chambers 112 may have a fluorescent compound that is configured to react with a different biomarker of interest. This may allow multiple biomarkers to be evaluated simultaneously. In other cases, some or all of the reaction chambers 112 may use the same fluorescent compound.

The fluorescent compound used in sample processing device 110 can be excited by light with a wavelength that falls within an excitation band for that compound. In response to being excited, the fluorescent compound can emit light in an emission band that is not identical to the excitation band.

In some embodiments, the sample processing device 110 may include a microfluidic chip. The microfluidic chip may include one or more reservoirs that define the reaction chambers 112. The microfluidic chip may include capillary pathways that direct an acquired sample to the reaction chambers. Each reaction chamber 112 can have a fluorescent compound positioned therein to react with a sample that is acquired by sample processing device 110.

As shown in system 100, each reaction chamber 112 can have a separate emission window 114. When the sample processing device 100 is positioned adjacent to, or contacting, the light guide unit 120, the emission windows 114 can be positioned to face the first end 124 of the light guide unit 120.

The illumination source 150 can be positioned to face the sample processing device 110. The illumination source 150 can include an emission location or aperture 152 that directs light at the sample processing device 110. The illumination source 150 can be configured to emit light within the excitation band of the fluorescent compound used in sample processing device 110.

The excitation light emitted from the illumination aperture 152 can be directed to the reaction chambers 112. For example, the sample processing device 110 may act as a waveguide to direct the excitation light to the reaction chambers 112. In some cases, the illumination source 150 may be positioned facing the side of the sample processing device 110, rather than directing light at the sample processing device 110 from free space.

When the fluorescent compounds in the reaction chambers 112 are excited by light in the excitation band, the emitted light passes through the emission windows 114 to the light guide unit 120. The light guide unit 120 can transfer the emitted light to the imaging detector 140.

Imaging detector 140 can be configured to measure the intensity of the light incident on its input surface 142. The imaging detector 140 can include an array with a plurality of distinct spatial areas. The imaging detector 140 may be operable to measure the intensity of light received in each spatial area. Each of these spatial areas may define a pixel of the imaging detector 140.

The light guide unit 120 can include a transfer/transmission section that may constrain the angular displacement or spread of the light from the reaction chambers 112 to ensure that the intensity of light from the different chambers is independently measurable.

The light guide 120 can be configured to transfer light emitted from the fluorescent compound in the reaction chambers 112 to the imaging detector 140. A first end 124 of the light guide 120 can be attached to the sample processing device 110.

When the sample processing device 110 is attached to the light guide 120, the emission windows 114 of the reaction chambers can be positioned to face the first end 124. The second end 126 of the light guide can be attached to the imaging detector 140.

The first end 124 of the light guide 120 can be bonded to the sample processing device 110 to transfer the light emitted from the reaction chambers 112 to the imaging detector 140 at the second end 126. In some cases, the light guide 120 may be attached to the sample processing device 110 using an index matching gel or an optical adhesive. This may secure the sample processing device 110 to the light guide 120 to allow the reaction chambers to be tested.

The first end 124 of the light guide 120 may be detachably attached to the sample processing device 110. For instance, in some embodiments the sample processing device 110 may be in the form of a disposable cartridge. The sample processing device 110 can be optically coupled to the first end 124 while the collected sample is imaged. In some cases, the sample processing device 110 can be positioned to contact the first end 124 while imaging is occurring.

The sample processing device 110 may subsequently be discarded following imaging. In some cases, the remainder of system 100 may then be re-used to image a different sample processing device 110.

In general, the light guide unit 120 can include a filter section configured to restrict the light that reaches the imaging detector 140 that is not the result of an emission from the fluorescent compound. The light guide unit 120 can be configured to reduce, or eliminate, the excitation light that passes through to the imaging detector.

The light guide unit 120 can include an optical filter 130 with a stop-band defined based on the excitation wavelength. The optical filter 130 can be defined to allow light in the emission band, or at least a portion of the emission waveband, to pass therethrough. For instance, the passband of the optical filter 130 can be defined to include the emission peak of the fluorescent compound while blocking light from some of the emission band.

The optical filter 130 can be defined based on a series of phase shifts and/or amplitude reflects. The phase shifts and amplitude reflections can interfere constructively and destructively to transmit or block light dependent on the wavelength of the light and its angle of incidence. The plurality of phase shifts can be defined using a multilayer optical coating, an embedded Bragg grating, or as part of a photonic crystal slab for example.

The light guide 120 can also be configured to limit the angular spread of light emitted from the reaction chambers 112 that is passing towards the imaging detector 140. This can prevent excessive overlap of the light from different reaction chambers 112 and thus allow the detection of differences in intensity of light between nearby chambers 112.

The light guide unit 120 may define an angular light acceptance range. The light guide unit 120 may prevent light that from entering when it is incident at an angle outside the angular light acceptance range. In some case, the angular light acceptance range may vary based on the fluorescent compound used. However, in general, where the excitation band and emission band are close, or even partially overlap, a narrow acceptance range may be used. For instance, the light guide unit 120 may only allow light to enter from an angle of less than about 20 degrees. The specific configuration of the filter 130 and angular light acceptance range may be adjusted based on the wavelength of light emitted by illumination source 150.

The filter 130 can be configured to prevent light with the excitation wavelength from passing therethrough. Additionally, the angular light acceptance range may further reduce the amount of excitation light that can enter light guide unit 120, particularly where the illumination source 150 is arranged to emit light at an angle to the direction in which the first end 124 is facing.

Limiting the angular light acceptance range may also provide a sharper filtering operation, as the cut-off wavelength of filter 130 can shift with the incidence angle. By limiting the permitted angle of incidence, excitation light that otherwise might be able to pass through filter 130 can be prevented from reaching the detector 140.

In some embodiments, the light guide unit 120 may include a plurality of fiber-optic cables 122. The plurality of fiber-optic cables 122 can be arranged in an array, with each fiber-optic cable 122 extending from the first end 124 of the light guide unit 120 to the second end 126 of the light guide unit 120.

The array of fibre-optic cables 122 may be formed as a bundle of unclad fibre-optic glass. The bundle can be heated and then cooled to shrink into a single piece of glass. The ends of the bundle can be severed and then polished before use in the light guide unit 120.

For example, a bundle of fibre-optic cables where each fibre-optic cable is less than 10 micrometres may be used. In some embodiments, the fibre-optic cables may be about 6 micrometers in diameter and the bundle may be in the range of about 10 mm-15 mm in length from the first end 124 to the second end 126, for example 13 mm.

In some embodiments, the light guide unit 120 may direct a plurality of independent light signals to the imaging detector 140. Each light signal may be directed to a distinct spatial area. These signals may then be measured on an array of independent pixels by the imaging detector 140.

For example, in embodiments using an array of fiber-optic cables 122, each cable 122 can transfer a light signal to the imaging detector. Each fiber-optic cable may provide light to an individual pixel on the detector 140. All the light passing through that cable 122 may be measured on the same pixel. The detector can then output the intensity received in each pixel to an associated controller and/or electronics board.

In some cases, there may not be a one-to-one correspondence between fibers 122 and the separate pixel regions of the imaging detector 140. In some embodiments, the imaging system 100 can include a plurality of fibers 122 and imaging detector 140 pixel regions arranged to face each reaction chamber 112. This may facilitate alignment of the imaging detector 140, light guide unit 120 and sample processing device 110.

Light entering each fiber-optic cable 122 can be prevented from overlapping with light in the adjacent fiber-optic cables 122 as it travels to the imaging detector (i.e. by the walls of the fiber-optic cables). Thus, the imaging detector 140 may measure the intensity of light passed by each fiber-optic cable 122 independently.

In some cases, the light passed by multiple fiber-optic cables 122 may be directed towards the same spatial region of the imaging detector 140 and may thus be measured together.

The second end 126 of the light guide unit 120 can be positioned in close proximity to the imaging detector 140. In some embodiments, the second end 126 may be at most 100 micrometers from the imaging detector 140. The second end 126 can be positioned 50 micrometers or less from the imaging detector 140 in some cases. In some cases, the second end 126 may be positioned about 10 micrometers or so from the imaging detector 140. This may prevent, or reduce, overlap between the light that exits the light guide unit 120 from adjacent fiber-optic cables 122.

The width of the fiber-optic cables 122 can be defined to be substantially less than the width of the emission windows 114 (and the spacing between different emission windows 114). For instances, the fiber-optic cables 122 may have a diameter of less than about 10 micrometers.

The fiber-optic cables 122 may range in length from about 10 mm to upwards of about 100 mm (approximately 4 inches). The surface area of each emission window 114 facing the light guide unit 120 may be at least ten times greater than the open area of each optical fiber cable 122 at the first end 124. This may ensure that individual fiber-optic cables 122 transmit primarily, or entirely, light emitted from only one of the reaction chambers 112. In some cases, the diameter of the fiber-optic cables 122 may be narrowed or broadened to create a magnified or de-magnified image between different size emission windows 114 and spatial detection regions on detector 140.

The fiber-optic cables 122 can be selected with a defined numerical aperture. The numerical aperture may be selected to restrict the angular light acceptance range of each fiber-optic cable 122. The light entering each fiber-optic cable 122 can then be prevented from spreading angularly by the walls of the fiber-optic cable, thus preventing light in the adjacent cables from overlapping.

In some embodiments, the fiber-optic cables 122 may have a numerical aperture that is defined to allow light to enter the fiber-optic cables only from an angle of less than about 20 degrees. Light incident on the fiber-optic cables 122 from an angle of more than 20 degrees may thus be prevented from entering the fiber-optic cables 122. For example, in some cases, the numerical aperture of the fiber-optic cables 122 may be defined to be in the range of about 0.25-0.45. In some cases, the numerical aperture of the fiber-optic cables may be defined to be about 0.35.

The light guide unit 120 can also be positioned in close proximity to the reaction chambers 112. For instance, the light guide unit 120 may contact the emission windows 114 of the reaction chambers 112 when the sample processing device 110 is positioned for testing. This may further reduce the spread of light emitted by the reaction chambers 112.

In some embodiments, such as the example shown in FIG. 3, the optical filter 130 can be defined using a plurality of optical coating layers 132, 134, 136 deposited between the reaction chambers 112 and the imaging detector 140. The optical coating layers 132, 134, and 136 can be selected to define an optical passband that corresponds at least partially to the wavelength of the light emitted by the fluorescent compound.

The optical filter 130 can be provided using alternating coating layers 132, 134, 136 with different refractive indices. The interfaces between layers 132, 134, 136 can produce phased reflections that interfere with certain wavelengths of light and reinforce other wavelengths of light. Although only three coating layers 132, 134, 136 are shown, it should be understand that varying numbers of layers may be used to provide the desired filter passband.

By controlling the thickness and number of the layers, the wavelength of the passband of the filter 130 can be tuned and made as wide or narrow as desired based on the resultant interference patterns. For instance, layers may be deposited with thicknesses in the range of about ¼ wavelength and ½ wavelength.

The individual layers 132, 134, 136 may be as thin as about 100 nm-200 nm for wavelengths in the range of about 650 nm. In many embodiments, a maximum of about 50 layers may be reasonably expected with more typical coatings in range of <25-30 layers.

In general, the total combined thickness 138 of all the coating layers (such as coating layer 132, 134, 136) can be less than 20 micrometers. In some cases, the thickness may be less than 10 micrometers. This may reduce the spread of light as it travels through filter 130, in particular as compared to glass plate filters that may be as thick as 1 mm or more.

For instance, the thickness 138 of the optical filter 130 provided using a stack of optical coatings can be 20 micrometers or less. The thickness 138 of the optical filter may be less than 10 micrometers in some embodiments. In some cases, the thickness 138 of the optical filter 130 can be 5 micrometers or less.

In the example of FIGS. 1-3, the coating layers 132, 134 and 136 are shown deposited directly on the second end 126 of the fiber-optic cables 122. Alternatively, the optical filter 130 may be provided by coating layers deposited on various other surfaces within imaging system 100 between the reaction chambers 112 and the input side of the imaging detector 140.

The coating layers 132, 134, 136 may include layers of dielectric coatings and/or metallic coatings. The coating layers 132-136 may be arranged as a stack with alternating high and low indices. For instance, for a passband in the range of about 650 nm the coating layers may include materials such as Hafnia, silica, or oxides. Differential materials may be used to provide the coating layers when the passband is in a different wavelength region.

The coating layers may be deposited using various thin film deposition methods, such as vapor deposition. For instance, the bundle of fiber-optic cables 122 may be positioned in a vacuum chamber over a source while the source is evaporated.

The duration over which the cable bundle is positioned in the vacuum chamber can be adjusted based on the desired thickness of the layer. The various coating layers can be selected so that the cumulative interference coefficients add up at a particular wavelength of interest.

Figure 4:
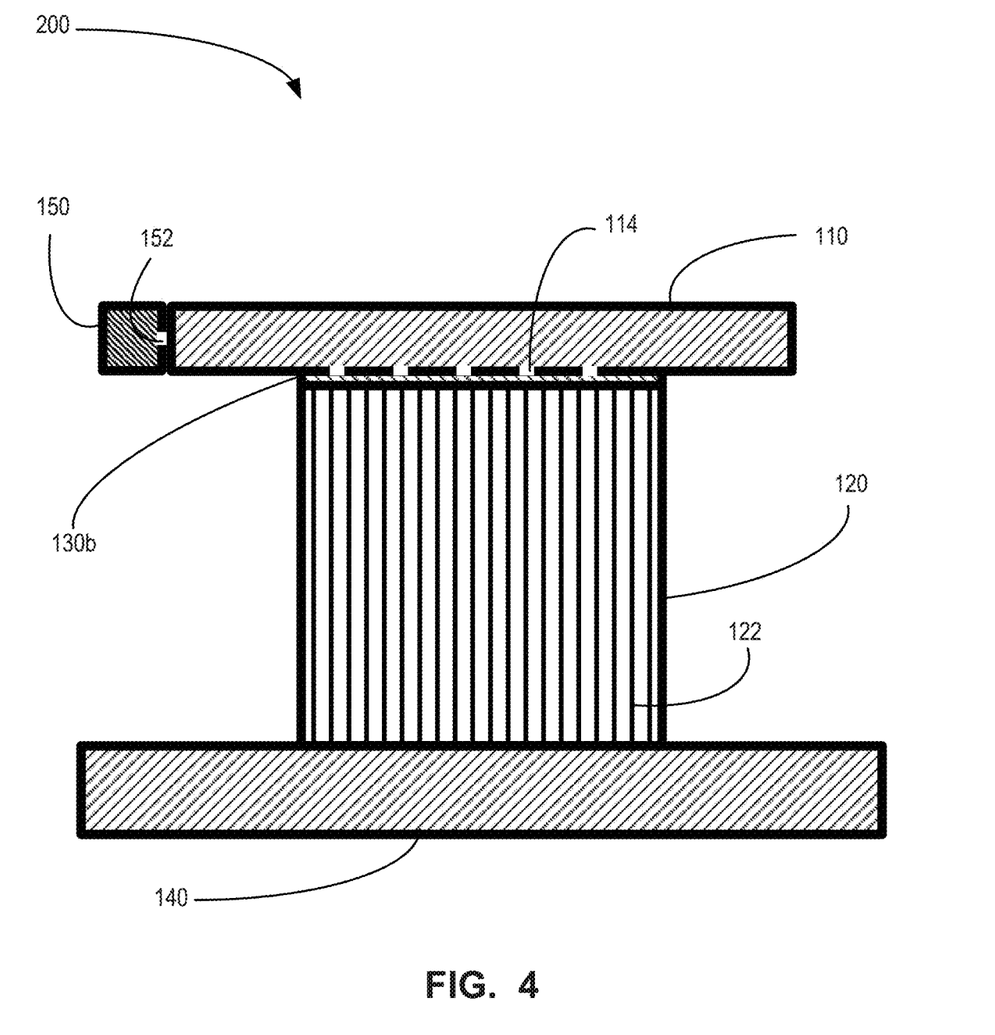
FIG. 4 is a sectional side view of another example imaging system in accordance with an embodiment.

In some embodiments, the optical filter 130b may be provided by optical coatings deposited on the first end 124 of the fiber-optic cables 122, as shown in FIG. 4. This may reduce the amount of unwanted light entering the light guide unit 120 (as compared to filtering after light has passed through some or all of the light guide unit 120), which may result in greater resolution at detector 140.

Figure 5:
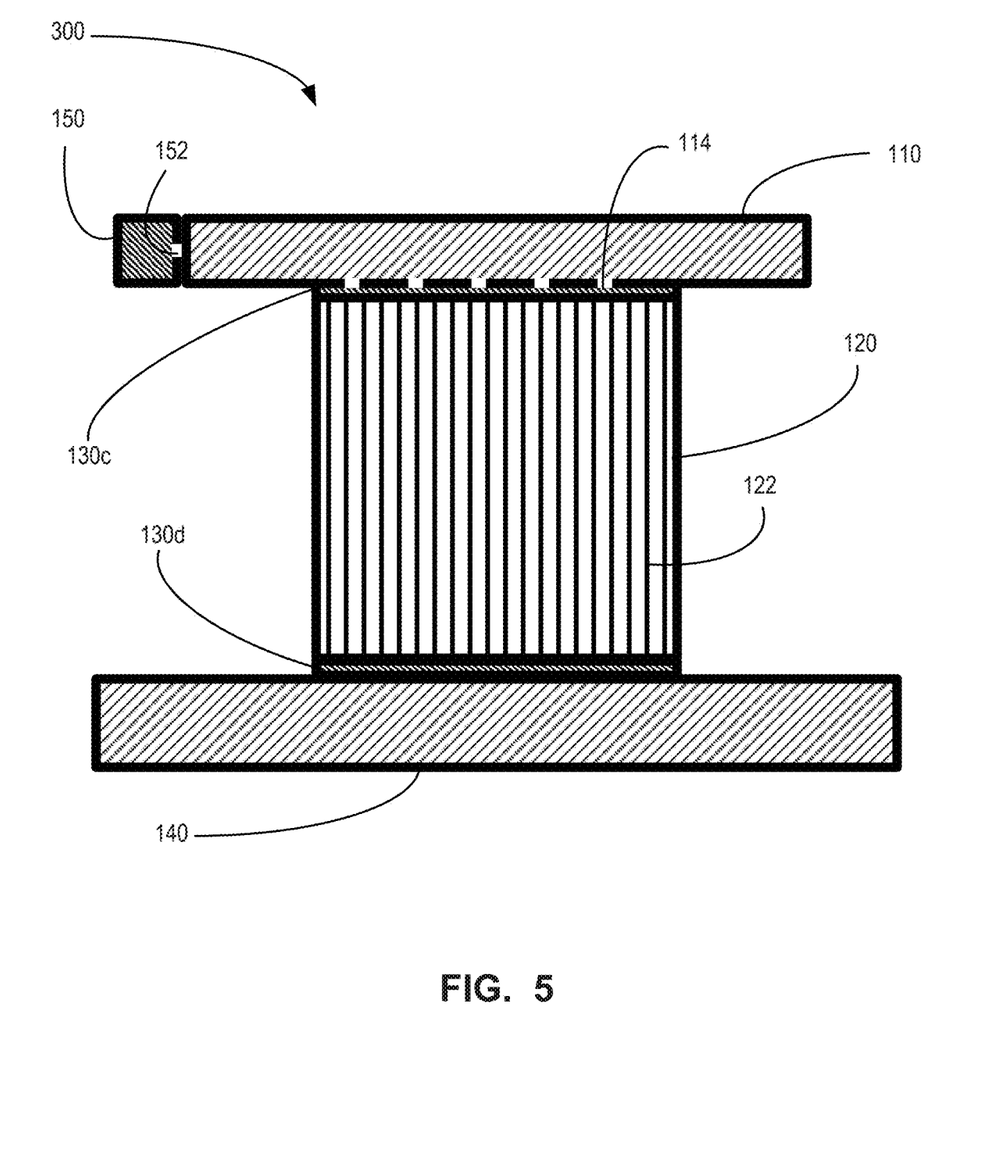
FIG. 5 is a sectional side view of another example imaging system in accordance with an embodiment.

In some embodiments, the optical filter 130 may be provided by optical coatings 130c/130d deposited on both the first end 124 and the second end 125 of the fiber-optic cables 122 as shown in FIG. 5. This may provide additional blocking of light from the excitation band.

In some cases, the optical filter 130 may also be provided by a coating deposited on the input side of the imaging detector 140. In some cases, the optical filter 130 may even be provided by a coating deposited on the emission windows 114 of the sample processing device 110.

In some embodiments, the optical filter may be integrated into the transmission portion of the light guide unit 120. For instance, a band pass filter may be incorporated directly into the fiber-optic cables 122. Each fiber-optic cable 122 may have a Bragg filter embedded therein. The passband of Bragg filter can be defined in a manner similar to optical filter 130 to reduce the amount of excitation light that can pass through to detector 140. This may further reduce the spacing between the fiber-optic cables 122 and the reaction chambers 112 by eliminating any separation that may be caused by optical coatings 132, 134, 136.

Figure 7:
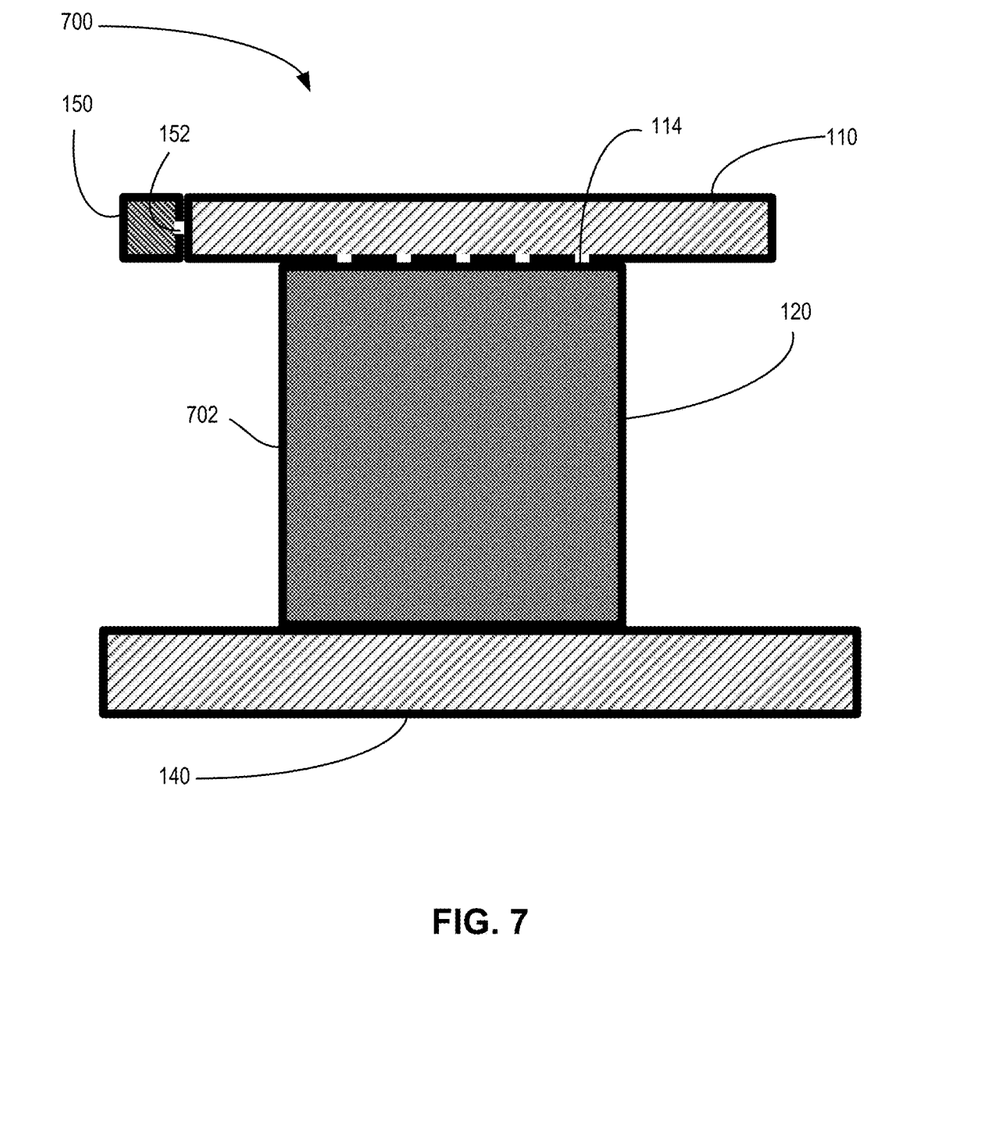
FIG. 7 is a sectional side view of another example imaging system in accordance with an embodiment.

In yet other cases, as shown in system 700 of FIG. 7, the light guide unit 120 may include a photonic crystal slab 702. The photonic slab 702 can be configured to constrain the angular speed of light passing therethrough. In some cases, the photonic crystal may be configured to define the optical filter and the angular light acceptance range. In such cases, the filter 130 and transmission guide may again be integrated within the light guide unit 120.

Various different types of fluorescent compounds may be used with sample processing device 110. The specific fluorescent compound used may vary depending on the specific application and/or biomarkers being tested. The emission bands and excitation bands can vary depending on the fluorescent compounds used. In general, however, the emission spectrum and excitation spectrum for the fluorescent compounds will be different (although there may be partial overlap).

For instance, in different embodiments the fluorescent compounds may have emission and/or excitation bands that range between the near-UV spectrum, the visible spectrum, and the near IR spectrum. Accordingly, the components of the imaging system 100 may be adjusted accordingly to ensure that the light guide unit 120 transmits light in the appropriate band, the filter 130 permits lights in the appropriate band to pass while preventing light in the excitation band from passing, the illumination source 150 is configured to emit light in the excitation band and the detector 140 is configured to capture the band of light emitted by the selected fluorescent compound.

For example, embodiments described herein may use fluorophores such as the Alexa Fluor fluorophores as the fluorescent compounds. For example, an Alexa Fluor 647 dye may be used. The Alexa Fluor 647 dye has an excitation band with an excitation peak near 650 nm and an emission band with an emission peak near 665-670 nm. The optical filter 130 can be configured to permit the emission peak to pass through the light guide unit 120 while preventing the excitation peak from passing therethrough.

The light guide unit 120 can also include an optical filter 130. The optical filter 130 can be configured as an optical band pass filter. The optical filter 130 may block light within the excitation wavelength from passing to the imaging detector 140 while passing light within at least a portion of the emission band.

In some cases, the emission band and the excitation band of the fluorescent compound may partially overlap. Accordingly, the optical filter 130 may prevent a portion of the excitation band from passing therethrough to ensure that little or no excitation light contaminates the intensity measurements of the imaging detector 140. The optical filter 130 can also be configured to provide a sharp contrast between the passband and the stopbands. The sharp contrast of optical filter 130 may be limited to a narrow range of incident angles, for instance up to 20 degrees. Accordingly, by controlling the angle at which light can enter the light guide unit 120, the contrast of the optical filter 130 can be increased.

The relationship between the excitation band and the emission band can vary with the specific fluorescent compound chosen. The excitation wavelength of illumination source 150 and the characteristics of optical filter 130 may be selected based on the efficiency curve of the particular fluorescent compound being used.

The fluorescent compounds used in the sample processing device 110 may have a limited excitation bandwidth. Accordingly, the illumination source 150 can be selected to emit light that falls within the excitation bandwidth. For instance, the wavelength emitted by the illumination source 150 can be selected based on the excitation peak of the fluorescent compound.

In some cases, the excitation bandwidth may overlap with the emission bandwidth of the fluorescent compound. Typically, however, the excitation peak of the fluorescent compound will be offset from the emission peak of the fluorescent compound (even if the emission peak falls within the excitation bandwidth). The light emitted from the illumination source 150 can be selected to fall within the excitation bandwidth while avoiding the emission peak of the fluorescent compound.

In some embodiments, the illumination source 150 may be a broad waveband LED source. In such embodiments, the wavelength of light emitted by the illumination source 150 may be shifted further from the emission peak (and also possibly further from the excitation peak) to ensure that the excitation light does not interfere with the emitted light that should be passed by filter 130.

In other embodiments, the illumination source 150 may include a narrow-band laser diode. The light emitted by the illumination source 150 may then be focused to the excitation peak, or near to the excitation peak, with reduced risk of interfering with the peak of the emission spectrum.

In some embodiments, rather than directing light from free space onto the sample processing device 110, the illumination source 150 can direct light into the side of the sample processing device 110. The sample processing device 110 may then direct the light to the reaction chambers 112 to excite the samples being testing. Optionally, an optical filter may be provided between the illumination source 150 and the sample processing device 110 to reduce or avoid contamination in the excitation light that impinges on the reaction chambers 112.

As shown in FIG. 2, the illumination aperture 152 can be positioned to face a side edge 116 of the sample processing device 110. The illumination aperture 152 is thus facing in a direction that is perpendicular to the direction in which the input surface 142 of the detector 140 is facing (and the direction in which first end 124 of the light guide unit 120 is facing).

The imaging system 100 may also include a controller coupled to the detector 140 and the illumination source 150. The controller may be implemented using a micro-controller, FPGA or application specific circuitry. In some cases, the controller may be implemented using a processor coupled to the imaging detector 140 and illumination source.

The controller may be configured to activate the detector 140 and the illumination source 150 in a synchronized manner. For instance, an emission flash from the illumination source 150 may be triggered synchronized with a frame capture by the detector 140. This may facilitate measuring the light emitted by the fluorescent compounds in response to the excitation light.

Figure 6:
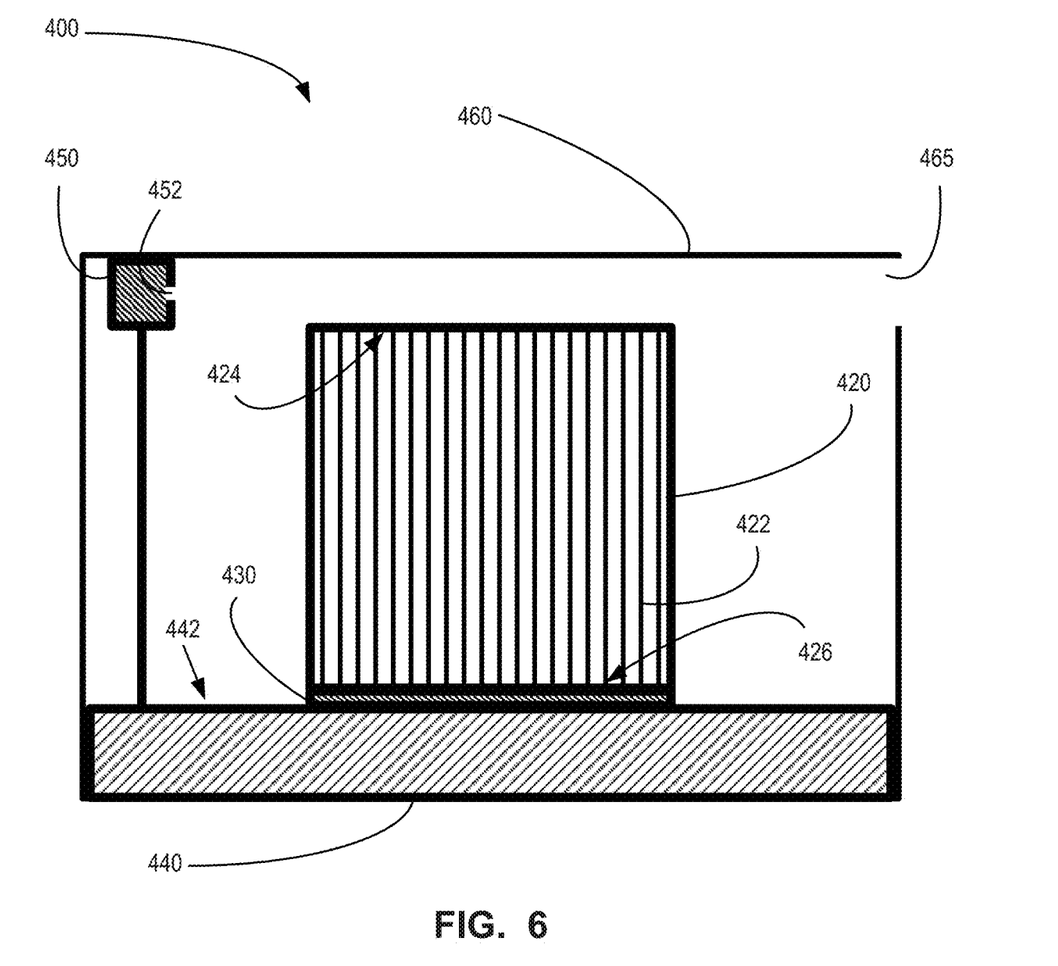
FIG. 6 is a sectional side view of an example portable imaging apparatus in accordance with an embodiment.

Referring now to FIG. 6, shown therein is an example of a portable imaging apparatus 400. The portable imaging apparatus 400 is an example of an imaging apparatus that may be used in embodiments of systems 100, 200 and 300. The portable imaging apparatus 400 may be an example of a reusable imaging apparatus that is usable with a sample processing device such as sample processing device 110.

As shown in FIG. 6, the portable imaging apparatus 400 includes a light guide unit 420 that includes an optical filter 430. The light guide 420 and optical filter 430 may be implemented in a manner analogous to light guide unit 120 and optical filters 130, 130b, 130c and 130d shown in FIGS. 1-5 and described herein above.

Portable imaging apparatus 400 can also include an imaging detector 440 and illumination source 450. The imaging detector 440 can be configured to detect an intensity of light incident on its input side 442. The imaging detector 440 may be implemented in a manner analogous to imaging detector 140 described herein above.

The illumination source 450 can be configured to emit from aperture 452 excitation light having an excitation wavelength that falls within the excitation band of a fluorescent compound used in a sample processing device, such as sample processing device 110. The illumination source 450 may be implemented in a manner analogous to illumination source 150 described herein above.

The light guide unit 420 extends from a first end 424 to a second end 426. The second end 426 is optically coupled to the input side 442 of the imaging detector 440. As with light guide unit 120, the light guide unit 420 can be configured to define a limited angular light acceptance range. The light guide unit 420 can also constrain angular spreading of light that may enter the first end 424 of the light guide unit 420. In the example shown, the light guide unit 420 includes a plurality of fiber-optic cables 422.

The light guide 420 includes an optical filter 430 that is configured as an optical band pass filter. The optical filter 430 can be configured to block light with a wavelength that corresponds to the excitation wavelength emitted by the illumination source 450 while passing light within at least a portion of the emission band of the fluorescent compound being assessed.

In the example shown, the filter 430 is positioned between the second end 426 of the light guide unit 420 and the input side 442 of the imaging detector 440. Filter 430 may be provided as a stack of optical coatings.

Additionally or alternatively, the filter 430 may also be positioned at the first end 424 of the light guide unit 420.

In some cases, the filter 430 may be embedded within the transmission portion of the light guide unit 420, for instance as Bragg filters embedded within optical fibers 422.

Additionally or alternatively, the light guide unit 420 may include a photonic crystal slab that may be configured to provide an optical filter. In such cases, the optical fibers 422 can be omitted. In some such cases, no coating may be required.

The portable imaging apparatus 400 can be arranged to receive a sample processing device such as sample processing device 110. In general, the sample processing device can include one or more reaction chambers for receiving a sample. The sample processing device also includes a fluorescent compound that can react with a received sample. The fluorescent compound can be excited by light with a wavelength that falls within an excitation band and emits light with a wavelength in an emission band in response to being excited.

The portable imaging apparatus can be arranged to receive the sample processing device with the first end 424 of the light guide unit 420 optically coupled to the reaction chamber or chambers. The first end 424 of the light guide unit 420 can be arranged to face the reaction chambers, and may even contact the reaction chamber(s). The portable imaging apparatus 400 can also be configured such that, when the sample processing device is received, the illumination source can be positioned to direct at least a portion of the excitation light to the reaction chamber.

As shown in FIG. 6, the portable imaging apparatus 400 can be arranged to receive the sample processing device with the first end 424 of the light guide unit 420 optically coupled to a reaction chamber on a front side of the sample processing device and the illumination source 450 optically coupled to a lateral side of the sample processing device. The sample processing device may be detachably attached to the light guide unit 420, for instance using an optical adhesive or an index matching gel.

As shown, the first end 424 of the light guide unit 420 (and, in turn the input side 442 of the detector 440) faces in a direction perpendicular to the direction in which the illumination aperture 452 is facing. The light emitted by illumination source 450 may thus be directed perpendicular to the face of the first end 424 of the light guide unit 420 and to the face of the input side 442.

The illumination source 450 can be mounted to a controller board. As shown in FIG. 6, the controller board can also include the detector 440. The controller board can support the illumination source 450 with the illumination aperture facing in a direction perpendicular to the direction in which the input side of the detector 440 is facing.

When a sample processing device is coupled to the imaging apparatus 400, the illumination source 450 can be aligned with, and facing, a lateral side edge of the sample processing device. For example, as shown in FIG. 6, the portable imaging apparatus 400 may be substantially enclosed with a housing 460.

The housing 460 may include an opening or slot 465 shaped to receive a sample processing device. The sample processing device can be translated through the slot 465 until it contact the illumination source 450 and the reaction chambers are positioned facing the light guide unit 420. Typically, the sample processing device can be inserted after a sample has been collected and processed using a fluorescent compound. Although the slot 465 is shown in a side of the housing 460, in alternative embodiments, the sample processing device may be inserted from another position such as the top of housing 460.

When a sample processing device is positioned in portable imaging apparatus 460, a user may operate a switch to activate the illumination source 450 and the imaging detector 440. This may synchronize the emission of light from the illumination source 450 with the image capture of imaging detector 440.

The bonded fluorescent compounds in the reaction chambers can emit light isotropically in the emission band in response to the excitation light from the illumination source. The emitted light can be transferred to the imaging detector 440 via the light guide unit 420, where the received intensity is measured. The intensity of the emitted light can be proportional to the concentration of the target bio-marker within a given reaction chamber. An evaluation of the bio-marker concentration may then be determined based on the measured light intensity.

Embodiments described herein may provide a compact and portable fluorescent imaging system and apparatus. The imaging system and apparatus can be used to quantify biomarkers within a sample processing device such as a microfluidic chip. The portable imaging apparatuses may be used for various applications, such as roadside saliva or blood testing for drug residues and fast portable medical screening for various disease markers that can be fixed to an antibody. The portable imaging apparatus of the embodiments described herein may enable miniaturization of medical bio-analyzers, which may facilitate health monitoring particularly in remote locations, such as on-board spacecraft or the International Space Station.

The portable imaging system and apparatus described herein may facilitate imaging of fluorescent compounds from reaction chambers without the need for re-imaging optics. This may avoid the need for precision lenses that could increase the size of the device substantially.

Embodiments described herein can provide a light guide unit that incorporates an optical band pass filter that targets an emission band of interest. The optical filter can be implemented with little to no increase in the size of the light guide unit, for instance with thin optical coating stacks or integrated Bragg filters. This can provide direct transfer of the emitted photons from the fluorescent compounds to the imaging detector with minimal loss of resolution. The optical filter can also prevent the excitation light from exciting the pixels of the imaging detector, further improving the resolution of the device.

The light guide unit described in embodiments herein can provide an interface between the imaging detector and the sample processing device being evaluated. The light guide unit may provide flexibility in the use of various imaging detectors that may be unable to contact a sample processing device directly (e.g. as a result of electronic chips and/or pins protruding from the device surface). The light guide unit may also allow a variety of sample processing devices and reaction chambers to be used, for instance ensuring that a thin optical filter is provided where the reaction chamber surface is unsuitable for a stack of optical coatings (e.g. where the reaction chamber is a flexible polymer).

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. An imaging system comprising:
  a sample processing device having a front side, a back side, and a lateral side, the sample processing device comprising at least one reaction chamber configured to receive a sample and a fluorescent compound usable to react with the sample, wherein each reaction chamber has an emission window at the front side of the sample processing device and the fluorescent compound is excitable by light with a wavelength that falls within an excitation band and the fluorescent compound emits light with a wavelength in an emission band in response to being excited;
  an illumination source optically coupled to the sample processing device, the illumination source having an emission aperture, the illumination source operable to emit excitation light through the emission aperture, the excitation light having an excitation wavelength that falls within the excitation band, wherein the illumination source and the sample processing device are arranged to direct at least a portion of the excitation light to the at least one reaction chamber;
  an image sensor operable to measure the intensity of received light; and
  a light guide having a first end optically coupled to the at least one reaction chamber, a second end optically coupled to the image sensor and an optical filter located between the at least one reaction chamber and the image sensor;
  wherein
  the first end of the light guide is positioned facing in a first direction towards the front side of the sample processing device and the emission aperture of the illumination source is positioned facing in a second direction towards the lateral side of the sample processing device, and the first direction and the second direction are orthogonal, such that the illumination source emits the excitation light towards the lateral side of the sample processing device whereby the excitation light propagates from the illumination source to the sample processing device along a light propagation path that is external to the light guide,
  the light guide defines an angular light acceptance range and is configured to constrain angular spreading of light entering the first end of the light guide, and
  the optical filter is configured to block light having the excitation wavelength that is emitted within the angular light acceptance range while passing light within at least a portion of the emission band.

2. The imaging system of claim 1, wherein the image sensor comprises an array that defines a plurality of distinct spatial areas, and the image sensor is operable to measure the intensity of received light in each of the spatial areas.

3. The imaging system of claim 2, wherein the light guide comprises an array of fiber-optic cables that extend from the first end to the second end, and each fiber-optic cable corresponds to one of the distinct spatial areas.

4. The imaging system of claim 3, wherein
  the at least one reaction chamber comprises a plurality of spaced apart reaction chambers; and
  each reaction chamber, of the plurality of spaced apart reaction chambers, faces at least one corresponding fiber-optic cable at the first end of the light guide.

5. The imaging system of claim 1, wherein the light guide comprises an array of fiber-optic cables that extend from the first end to the second end.

6. The imaging system of claim 5, wherein each fiber-optic cable has a numerical aperture that is defined to allow light to enter the fiber-optic cables only from an angle of less than about 20 degrees.

7. The imaging system of claim 5, wherein the optical filter comprises a Bragg filter embedded in each fiber-optic cable.

8. The imaging system of claim 1, wherein the optical filter comprises multiple layers of optical coatings.

9. The imaging system of claim 1, wherein the light guide comprises a photonic crystal that extends from the first end to the second end.

10. The imaging system of claim 1, wherein the at least one reaction chamber comprises a plurality of spaced apart reaction chambers, and the light guide is configured to constrain the angular spreading of light emitted from each reaction chamber within the angular light acceptance range to prevent the overlap of light from adjacent chambers.

11. The imaging system of claim 1, wherein the sample processing device comprises a microfluidic chip.

12. The imaging system of claim 1, wherein the first end of the light guide is detachably attached to the at least one reaction chamber.

13. A portable imaging apparatus usable with a sample processing device having a front side, a back side, a lateral side and a reaction chamber configured to receive a sample and a fluorescent compound usable to react with the sample, wherein the reaction chamber has an emission window at the front side of the sample processing device and the fluorescent compound is excitable by light with a wavelength that falls within an excitation band and the fluorescent compound emits light with a wavelength in an emission band in response to being excited, the portable imaging apparatus comprising:
an image sensor operable to detect an intensity of light incident on an input side of the image sensor;
an illumination source having an emission aperture, the illumination source operable to emit excitation light through the emission aperture, the excitation light having an excitation wavelength that falls within the excitation band;
a light guide extending from a first end to a second end that is optically coupled to the input side of the image sensor, the light guide defining an angular light acceptance range and being configured to constrain angular spreading of light entering the first end of the light guide; and
a housing containing the illumination source and the light guide, and the housing comprising a slot shaped to removably receive the sample processing device, the slot having a slot first side defined at the first end of the light guide, a slot second side defined at the illumination source, and a slot third side that includes an opening in an exterior of the housing, wherein the sample processing device is insertable into the slot through the opening;
wherein the first end of the light guide is positioned facing in a first direction towards the slot first side and the emission aperture of the illumination source is positioned facing in a second direction towards the slot second side, and the first direction and the second direction are orthogonal, such that when the sample processing device is positioned within the slot with the emission window at the slot first side and the lateral side of the sample processing device at the slot second side the illumination source is arranged to emit the excitation light towards the lateral side of the sample processing device whereby the excitation light propagates from the illumination source to the sample processing device along a light propagation path that is external to the light guide, and
the light guide includes an optical filter configured to block light having the excitation wavelength that is emitted within the angular light acceptance range while passing light within at least a portion of the emission band, and
the portable imaging apparatus is arranged to receive the sample processing device with the first end of the light guide optically coupled to the reaction chamber and the illumination source positioned to direct at least a portion of the excitation light to the reaction chamber.

14. The portable imaging apparatus of claim 13, wherein the image sensor comprises an array that defines a plurality of distinct spatial areas, and the image sensor is operable to measure the intensity of received light in each of the spatial areas.

15. The portable imaging apparatus of claim 14, wherein the light guide comprises an array of fiber-optic cables that extend from the first end to the second end, and each fiber-optic cable corresponds to one of the distinct spatial areas.

16. The portable imaging apparatus of claim 13, wherein the light guide comprises an array of fiber-optic cables that extend from the first end to the second end.

17. The portable imaging apparatus of claim 16, wherein the fiber-optic cables have a numerical aperture that is defined to allow light to enter the fiber-optic cables only from an angle of less than about 20 degrees.

18. The portable imaging apparatus of claim 16, wherein the optical filter comprises a Bragg filter embedded in each fiber-optic cable of the light guide.

19. The portable imaging apparatus of claim 13, wherein the optical filter comprises multiple layers of optical coatings.

20. The portable imaging apparatus of claim 13, wherein the light guide comprises a photonic crystal that extends from the first end to the second end.

21. The imaging system of claim 1, wherein the sample processing device is disposable.

22. The imaging system of claim 1, further comprising a housing containing the illumination source, the light guide, the image sensor, and a sample receiving volume within which the sample processing device is removably receivable.

* * * * *